(12) United States Patent
Piccin

(10) Patent No.: US 9,539,038 B2
(45) Date of Patent: Jan. 10, 2017

(54) INTRAMEDULLARY PIN

(71) Applicant: Nilli Del Medico, Orbassano (TO) (IT)

(72) Inventor: Katia Piccin, Borgio Verezzi (IT)

(73) Assignee: NILLI DEL MEDICO, Orbassano (TO) (IT)

( * ) Notice: Subject to any disclaimer, the term of this patent is extended or adjusted under 35 U.S.C. 154(b) by 43 days.

(21) Appl. No.: 14/418,530

(22) PCT Filed: Jul. 24, 2013

(86) PCT No.: PCT/IB2013/056049
§ 371 (c)(1),
(2) Date: Jan. 30, 2015

(87) PCT Pub. No.: WO2014/020488
PCT Pub. Date: Feb. 6, 2014

(65) Prior Publication Data
US 2015/0201978 A1    Jul. 23, 2015

(30) Foreign Application Priority Data

Jul. 31, 2012 (IT) .............................. TO2012A0687

(51) Int. Cl.
*A61B 17/72* (2006.01)
*A61B 17/88* (2006.01)
*A61B 17/92* (2006.01)

(52) U.S. Cl.
CPC ....... *A61B 17/7208* (2013.01); *A61B 17/7266* (2013.01); *A61B 17/8872* (2013.01); *A61B 17/921* (2013.01)

(58) Field of Classification Search
CPC ............ A61B 17/7208; A61B 17/7266; A61B 17/7258; A61B 17/7283
See application file for complete search history.

(56) References Cited

U.S. PATENT DOCUMENTS

| | | | | |
|---|---|---|---|---|
| 4,457,301 | A | * | 7/1984 | Walker ............................. 606/62 |
| 4,913,144 | A | | 4/1990 | Del Medico |
| 5,034,012 | A | | 7/1991 | Frigg |
| 5,116,335 | A | * | 5/1992 | Hannon et al. .................. 606/62 |
| 5,192,281 | A | * | 3/1993 | de la Caffiniere . A61B 17/7241 606/59 |
| 5,281,225 | A | | 1/1994 | Vicenzi |
| 5,618,286 | A | | 4/1997 | Brinker |
| 6,025,537 | A | * | 2/2000 | Werding et al. ........... 623/16.11 |
| 6,607,531 | B2 | * | 8/2003 | Frigg .............................. 606/62 |
| 6,783,530 | B1 | * | 8/2004 | Levy ............................... 606/63 |

(Continued)

FOREIGN PATENT DOCUMENTS

| | | |
|---|---|---|
| AT | 509852 B1 | 12/2011 |
| FR | 2656212 A1 | 6/1991 |
| WO | 95/12358 A1 | 5/1995 |

*Primary Examiner* — Jan Christopher Merene
*Assistant Examiner* — Atiya Mahmud
(74) *Attorney, Agent, or Firm* — Howson & Howson, LLP

(57) ABSTRACT

An intramedullary pin (1) is provided. The intramedullary pin has a self-locking distal end that can be used for treating metadiaphyseal fractures of long bones such as the humerus. Locking of the distal end of the intramedullary pin (1) can take place in a controlled and gradual, and also reversible, manner. The structure of the intramedullary pin (1) further allows the use of a guide wire, whereby the pin can be inserted into the fractured bone with the aid of a guide wire.

10 Claims, 3 Drawing Sheets

(56) References Cited

U.S. PATENT DOCUMENTS

| | | |
|---|---|---|
| 6,902,567 B2 | 6/2005 | Del Medico |
| 2005/0010225 A1 | 1/2005 | Del Medico |
| 2010/0087821 A1 | 4/2010 | Trip et al. |

* cited by examiner

INTRAMEDULLARY PIN

TECHNICAL FIELD

The present invention refers to an intramedullary pin. Particularly, the present invention refers to an intramedullary pin for treating metadiaphyseal fractures in long bones, such as the humerus.

PRIOR ART

The use of intramedullary pins for treating metadiaphyseal fractures of long bones such as the humerus, i.e. fractures of the diaphysis (the intermediate portion of the bone) that do not affect the proximal and distal proximal and distal epiphyses, is known.

In some intramedullary pins of the known type both ends of the pin need to be secured to the fractured bone by means of screws, which involves a long and highly invasive surgical intervention.

An equally long and invasive surgical intervention is then required when the pin must be removed.

In order to overcome this drawback, intramedullary pins were developed in the past that can be secured to the bone at a single end (proximal end), whereas the opposite end (distal end) is locked by itself within the bone.

An intramedullary pin with self-locking distal end is described for instance in U.S. Pat. No. 5,281,255.

With reference to FIGS. 1 and 2, the intramedullary pin 101 described in U.S. Pat. No. 5,281,255 comprises a head 103, suitable for being secured to the proximal epiphysis of the fractured bone by means of a screw 105, and a plurality of elastically deformable curved stems 107 secured at their proximal ends to said head 103.

Referring particularly to FIG. 1, the intramedullary pin 101 further comprises retaining means 109 arranged for bundling together the free ends 107a of the stems 107 and a tool 111 for driving the removal of said retaining means and the release of said end 107a of said stems 107.

The application of the intramedullary pin 101 is carried out essentially as follows: once the channel for receiving the pin 101 has been created, said pin is inserted into the fractured bone with the stems 107 bundled together by the retaining means 109; when the pin is in its correct position, by acting upon the tool 111 the retaining means 109 are removed and the ends 107a of the stems 107 are released; owing to their elasticity, said stems 107 spread apart pressing against the bone and thus realizing the anchoring of the distal end of the pin 101; at last, the head 103 is secured to the proximal epiphysis of the fractured bone by means of the screw 105.

When the fracture is consolidated, it is possible to extract the pin 101 from the proximal epiphysis by pulling the stems 107 out of the bone.

An intramedullary pin of this type, however, though solving the problems related to anchoring the pin at the distal end, is not free from drawbacks.

In the first place, if any problem of positioning arises during application of the pin after removal of the retaining means, the situation is irretrievable.

In the second place, as the stems have a remarkable length and are secured to the pin head solely at their proximal ends, the torques to which the distal ends of said stems are subjected upon their release are remarkable and cannot be controlled.

Finally, the intramedullary pin described above cannot be inserted into the bone with the aid of a guide wire, because the central longitudinal portion of said pin is already taken up by the tool driving the removal of the retaining means.

The object of the invention is to overcome the aforesaid drawbacks.

Particularly, the main object of the present invention is to provide an intramedullary pin with self-locking distal end which allows a controlled gradual locking of said distal end.

Another object of the present invention is to provide an intramedullary pin with self-locking distal end that can be inserted into a fractured bone with the aid of a guide wire.

These and other objects are achieved by the intramedullary pin as claimed in the appended claims.

DISCLOSURE OF THE INVENTION

Thanks to the fact that the free distal ends of the stems of the intramedullary pin according to the invention are retained by a slider and that said slider is able to slide by means of suitable driving means from the distal end to the proximal end of said stems, the release of said stems can take place in a gradual, controlled and reversible way. Similarly, the removal of the intramedullary pin from the bone after consolidation of the fracture can take place in a controlled, gradual way.

Advantageously, said slider comprises a central longitudinal through-hole for the passage of a guide wire.

Preferably, said slider has a small space requirement, especially in the radial direction. According to a preferred embodiment of the invention, said slider has an outer diameter not greater than the diameter of the bundle of stems of the pin according to the invention when said stems are in their retained position.

BRIEF DESCRIPTION OF THE DRAWINGS

Features and advantages of the invention will become more apparent from the following description of a preferred embodiment of the inventions, given merely by way of non-limiting example, with reference to the accompanying drawings, in which.

DETAILED DESCRIPTION OF A PREFERRED EMBODIMENT

Figure 1:
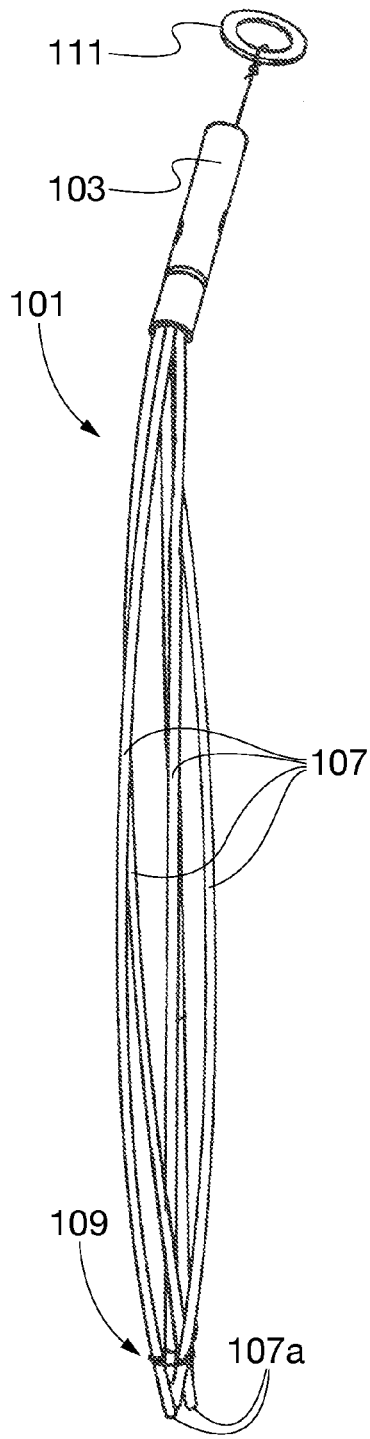
FIG. 1 shows an intramedullary pin of known type, illustrated in a first configuration or "closed" configuration.
Figure 2:
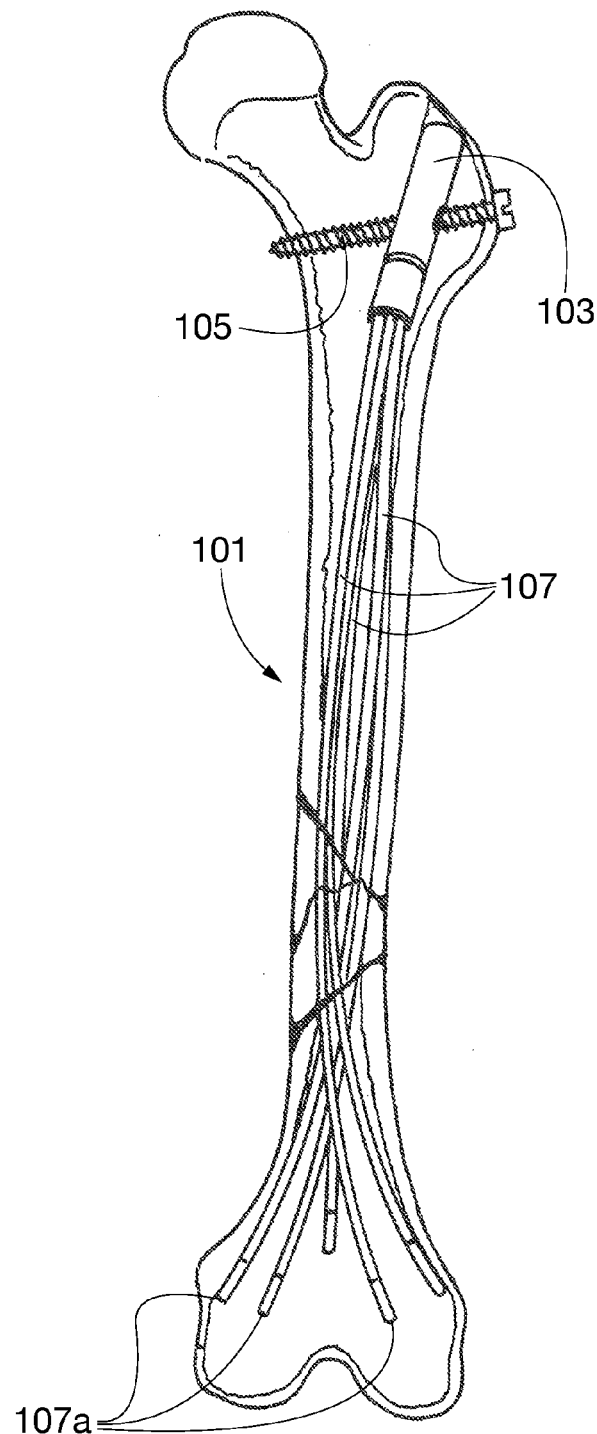
FIG. 2 shows the intramedullary pin of FIG. 1 in a second configuration or "open" configuration within a fractured bone.
Figure 3:
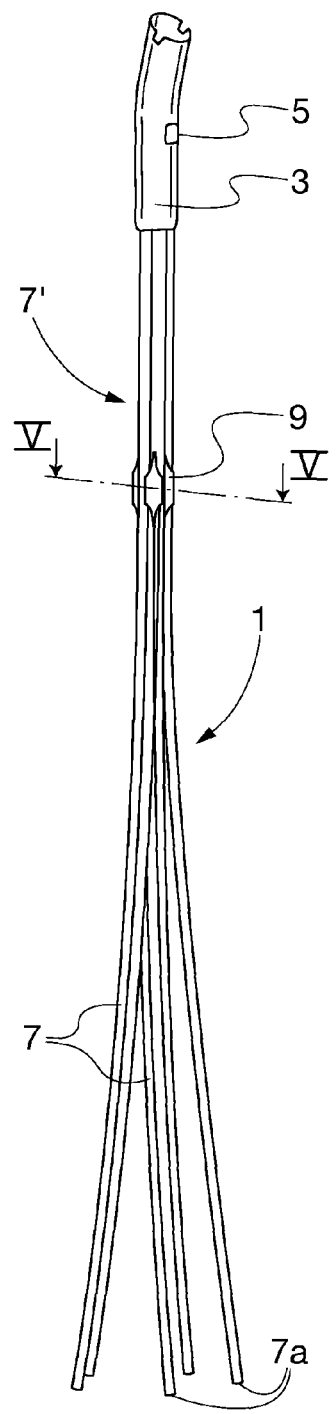
FIG. 3 shows an intramedullary pin according to the invention, illustrated in the "open" configuration.

With reference to FIG. 3, there is illustrated an intramedullary pin 1 according to the invention.

Said pin 1 comprises at its proximal end a head 3 provided with a bore 5 for the passage of a means for securing the pin to the proximal epiphysis od a fractured bone.

The pin 1 further comprises a bundle 7' of elastically deformable, slightly curved stems 7 departing at their proximal ends from the head 3, the distal ends 7a of said stems 7 being free. In the illustrated embodiment there are provided five stems 7, but it is clear that the bundle 7' might include a different number of stems 7.

Said stems 7 preferably have a circular cross-section and rounded distal ends 7a.

Said stems 7 are radially retained close to one another by using suitable retaining means.

In particular, according to the invention, the retaining means of the intramedullary pin 1 comprise a slider 9 able to slide along said bundle 7' of stems from their distal ends 7a to their proximal ends, i.e. to the head 3 of the pin 1, and vice versa.

Said slide 9, which will be described in detail below, comprises seats suitable for housing and retaining the stems 7, said seats being provided in a number at least equal to the number of said stems.

It will be apparent to the person skilled in the art that, owing to the fact that the stems 7 are constrained within the seats of the slider 9, along the portion comprised between the head 3 of the pin 1 and the position of the slider 9, the stems 7 will be held mutually adjacent, whereas along the portion between the position of the slider 9 and their distal ends 7a, the stems will be free to spread apart by virtue of their curved shape and their elastic deformability.

Figure 4:
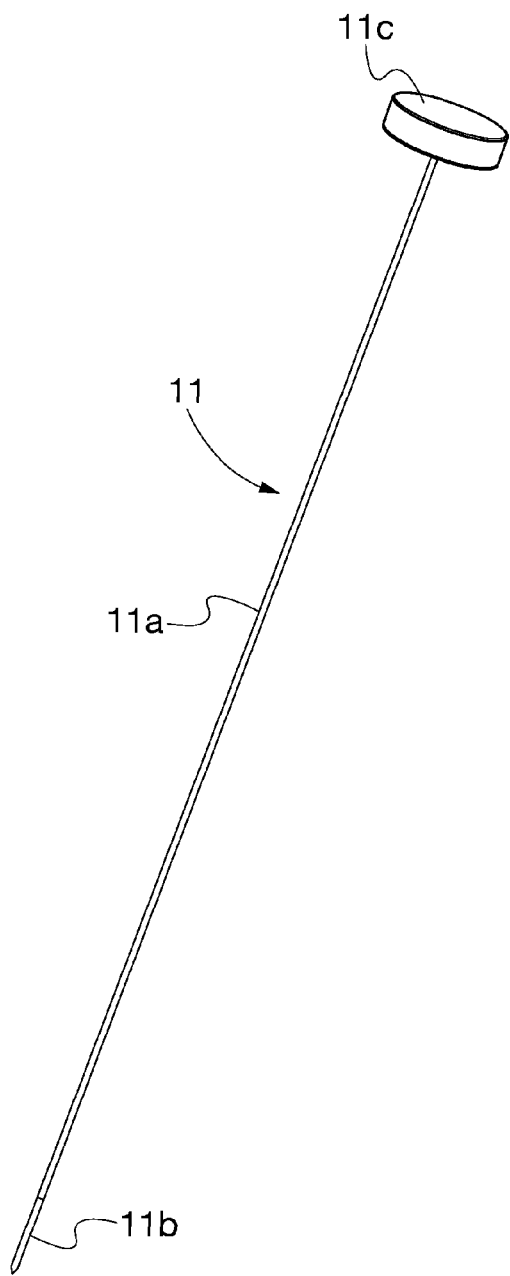
FIG. 4 shows the driving tool for the slide of the intramedullary pin of FIG. 3.

According to the invention, the position of the slider 9 along the bundle 7' of stems 7 can be advantageously adjusted in a controlled and gradual way thanks to the driving tool 11 illustrated in FIG. 4.

Said driving tool 11 comprises a shaft-like body 11a ending at its distal end with engaging means 11b suitable for engaging corresponding engaging means provided in the slider and at its proximal end with a handle 11c that can be grasped by the user (i.e. by the orthopedic surgeon) for altering—by means of the driving tool 11 itself—the position of the slider 9.

In the example shown, the engaging means of the driving tool comprise a threaded portion 11b suitable for engaging into a corresponding threaded hole provided in the slider 9. It will be apparent to the person skilled in the art that engaging means of a different kind might also be used, provided that they ensure the correct engagement between the driving tool 11 and the slider 9.

Figure 5:
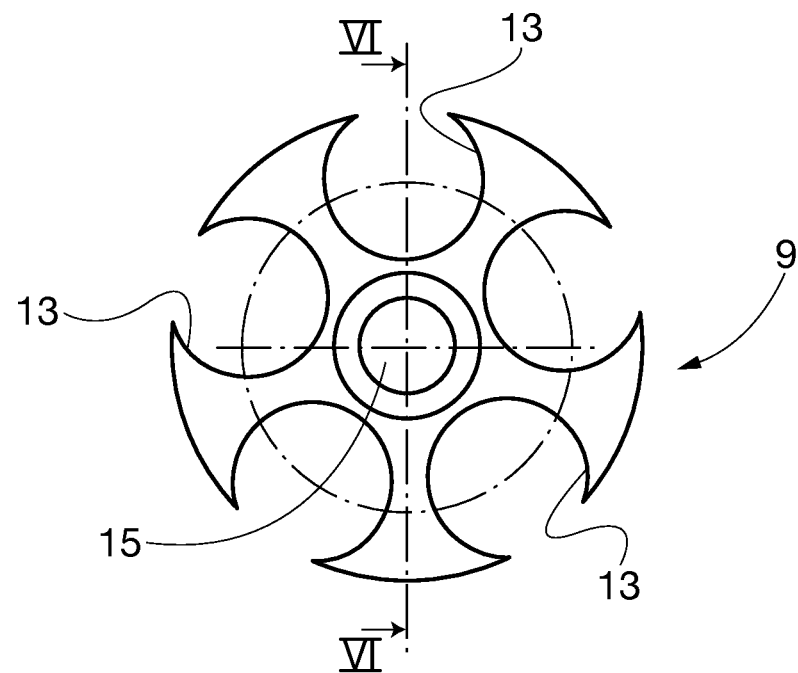
FIG. 5 is a sectional view along line V-V of the slider of the intramedullary pin of FIG. 3.
Figure 6:
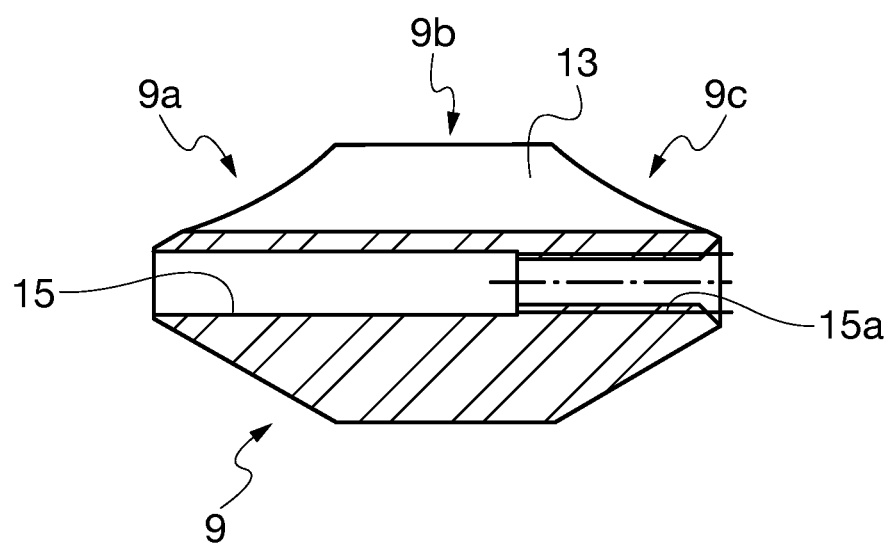
FIG. 6 is a sectional view along line VI-VI of the slider of FIG. 5.

The slider 9 is shown in detail in FIGS. 5 and 6. Said slider 9 has a body generally comprising a central portion 9b and tapered end portions 9a, 9c; the presence of said tapered portions facilitates sliding of the slider 9 along the bundle 7' of stems 7 in either direction.

As can be well seen in FIG. 5, the slider has a plurality of seats 13 for the stems 7 of the intramedullary pin 1. The slider 9 thus allows the stems 7 held within the seats 13 to be kept close to one another.

In the illustrated example, the slider 9 is made as a solid of revolution and the seats 13—in a number of five in the illustrated example—are provided along the outer circumference of the body of the slider 9 and are preferable arranged equally spaced along said circumference.

The seats 13 may have any shape suitable for firmly retaining in their inside the corresponding stems 7.

In the simplest embodiment, they may be made as longitudinal through-holes having circular cross-section with a diameter essentially equal to the one of the stems 7.

Such embodiment, though being simple, would however have the drawback in that it would make it compulsory to realize a slider 9 with a maximum outer diameter remarkably greater than the diameter of the bundle 7' of the stems 7.

It has to be noted that by diameter of the bundle 7' it is meant the diameter of the circumference circumscribing the bundle 7' of the stems 7 when these are kept mutually adjacent ("closed" configuration).

Because of the overall size of the slider 9, sliding thereof along the stems 7 might prove cumbersome.

Therefore, in the preferred embodiment shown in FIGS. 5 and 6 the seats 13 are made as cavities open on the outer surface of the body of the slider 9 and have a cross-section shaped as a circular segment.

In order for the stems 7 to be held reliably within the seats 13, said seats—at least along a longitudinal portion of the slider 9, i.e. at least along the central portion 9b of the slider 9—must have a diameter substantially equal to the one of said stems 7 and must be shaped in such a way that their walls, at the outer surface if the body of the slider 9, are convergent.

Therefore, the cross-section of the seats 13—at least along a longitudinal portion of the slider 9, i.e. at least along a central portion 9b of the slider 9—has the shape of a circular segment having a diameter substantially equal to the one of said stems 7 and with an angle greater than 180°, preferably comprised within 210° and 300° and even more preferably equal to approximately 270°.

In other words, the shape and size of the seats 13 are chosen so that the stems 7 received within the seats 13 are tangent to the outer surface of the body of the slider 9, at least along a longitudinal portion of said slider, i.e. at least along the central portion 9b of said slider.

Thanks to this measure, the provision of the slider 9 does not involve any increase in space requirement with respect to the bundle 7' of the stems 7 and its movements are facilitated.

The slider 9 further comprises a longitudinal through-hole 15 in a central position for the passage of a guide-wire, whereby the pin 1 according to the invention can advantageously be inserted into the fractured bone with the aid of a guide wire.

As can be well seen in FIG. 6, a portion 15a of the hole 15 is innerly threaded, so that it can become engaged with the threaded portion 11b of the driving tool 11 and ensure the correct coupling between said driving tool and said slider.

The parts of the pin 1 can be made of any material suitable for use in surgery; they can preferably be made of biocompatible steel such as AISI 316LVM, for instance.

The application of the intramedullary pin is effected essentially as follows:
  a channel is preliminarily obtained in the fractured bone;
  with the slider 9 being positioned at the distal ends 7a of the stems 7 (i.e. with the pin 1 in completely "closed" configuration) a guide wire is inserted through the through-hole 15 of the slider 9;
  with the aid of said guide wire, the pin 1 is inserted into the channel;
  the guide wire is pulled out of the channel 15 and in its place there is inserted the driving tool 11 in such a way that the threaded portion 11b of said driving tool engages with the threaded portion 15a of said hole 15;
  once the slider 9 is firmly coupled to the driving tool 11, the user, by exerting a pulling force on the handle 11c of said driving tool, can make the slider 9 slide along the bundle 7' of the stems 7 towards the head 3 of the pin 1, until the slider is brought to the desired position;
  as the slider 9 moves further away from the distal end of the pin 1, the distal ends 7a of the stems 7 spread apart;
  once the slider 9 is in the desired position it is possible to remove the driving tool 11 and secure the head 3 of the pin to the proximal epiphysis of the fractured bone.

Once the fracture has consolidated, the intramedullary pin 1 according to the invention can be removed in the following way:

the means retaining the head 3 of the pin 1 on the proximal epiphysis of the bone are removed;

the driving tool 11 is inserted so that the threaded portion 11b of said driving tool engages with the threaded portion 15a of the channel 15 of the slider 9;

once the slider is firmly coupled to the driving tool 11, the user, by acting on the handle 11c of said driving tool, can push the slider 9 so as to make it slide along the bundle 7' of the stems 7 until the slider is brought to the distal end 7a of the stems 7;

with the stems 7 having this "closed" configuration, the pin 1 can be easily removed from the bone.

It is clear from the above description that the intramedullary pin according to the invention attains the objects set forth above.

Indeed, the slider 9 can be moved in a gradual and controlled way along the bundle 7' of stems 7. Accordingly, the portion of the stems that is free to spread apart and move away from the stems is gradually modified.

Furthermore, the opening of the bundle 7' of the stems 7 is reversible, which is useful not only upon removal of the intramedullary pin 1, but also upon application of the pin itself, for instance in case of a positioning error.

Moreover, the slider 9 can be positioned in an intermediate position between the distal end and the head 3 of the pin 1, so that on one part the locking of the distal end of said pin is firm and on the other part the arm of the torques to which the stems 7 are subjected is limited.

Finally, the structure of the intramedullary pin 1 according to the invention makes it possible to use a guide wire during its introduction into the fractured bone.

It will be apparent to the person skilled in the art that the embodiment described and illustrated in detail has been provided merely by way of example and several modifications and variations can be made without departing from the scope of protection as defined by the accompanying claims.

The invention claimed is:

1. Intramedullary pin comprising:
a head;
a bundle comprising a plurality of stems having a slightly curved shape and being elastically deformable, each of said stems having a proximal end and a distal end, the proximal ends of said stems being fastened to said head and the distal ends of said stems being free;
retaining means for keeping said stems close to one another;
wherein said retaining means comprise a slider which is provided with seats suitable for housing and retaining said stems, said seats being provided at least in the same number as said stems, and which is able to slide along said bundle of said stems from the distal end to the proximal end thereof, and vice versa, whereby, between the proximal ends of the stems and a position of the slider, said stems are kept close to one another, whereas, between the position of the slider and the distal ends of the stems, said stems are free to spread apart by virtue of their curved shaped and elastic deformability,
wherein said slider has a body having a shape of a solid of revolution and said seats are provided along an outer circumference of said body, wherein said body comprises a central portion and tapered end portions, and wherein said body has a maximum outer diameter that is smaller than a diameter of a circumference circumscribing said bundle of said stems where said stems are kept close to one another at the position of the slider.

2. Intramedullary pin according to claim 1, wherein said seats are longitudinal cavities open at an outer surface of said body of said slider and wherein, at said outer surface, walls of said cavities converge.

3. Intramedullary pin according to claim 2, wherein a cross-section of said seats has a shape of a circular segment, with a diameter substantially equal to a diameter of said stems and an angle greater than 180°.

4. Intramedullary pin according to claim 1, wherein said angle is equal to about 270°.

5. Intramedullary pin according to claim 3, wherein said angle is within a range of 210° to 300°.

6. Intramedullary pin according to claim 1, wherein said intramedullary pin further comprises a driving tool for driving said slider to slide along said bundle of said stems and wherein said driving tool is provided with engaging means suitable for engaging corresponding engaging means provided in said slider.

7. Intramedullary pin according to claim 6, wherein said engaging means of said driving tool comprise a threaded portion and said engaging means of said slider comprise a corresponding threaded hole.

8. Intramedullary pin according to claim 7, wherein said slider comprises a longitudinal through-hole for passage of a guide wire and said threaded hole of the engaging means of said slider is a threaded portion of said longitudinal through-hole of said slider.

9. Intramedullary pin according to claim 1, wherein said slider comprises a longitudinal through-hole for the passage of a guide wire.

10. Intramedullary pin according to claim 1, wherein said seats are equally spaced along said outer circumference of said body.

* * * * *